United States Patent [19]
Hecht

[11] Patent Number: 5,571,690
[45] Date of Patent: Nov. 5, 1996

[54] METHOD FOR THE CELL-FREE SYNTHESIS OF PROTEINS

[75] Inventor: Sidney M. Hecht, Charlottesville, Va.

[73] Assignee: The University of Virginia Patents Foundation, Charlottesville, Va.

[21] Appl. No.: 696,916

[22] Filed: May 8, 1991

[51] Int. Cl.$^6$ .................................. C12P 19/34
[52] U.S. Cl. .................. 435/69.1; 435/68.1; 435/91.2
[58] Field of Search .................. 435/68.1, 91.2, 435/69.1

[56] References Cited

U.S. PATENT DOCUMENTS

| | | | |
|---|---|---|---|
| 4,683,195 | 7/1987 | Mullis et al. | 435/91.2 |
| 4,683,202 | 7/1987 | Mullis et al. | 435/91.2 |
| 4,761,375 | 8/1988 | Clark et al. | 435/240.2 |
| 4,800,159 | 1/1989 | Mullis et al. | 435/91.2 |
| 4,886,747 | 12/1989 | Derynck et al. | 435/69.4 |
| 4,945,052 | 7/1990 | Hardy et al. | 435/172.3 |

OTHER PUBLICATIONS

Spirin et al, *Science*, vol. 242, pp. 1162–1164, (1988).
Wilson et al, *Gene*, vol. 77, pp. 69–78, (1989).
Saiki et al, *Science*, vol. 239, pp. 487–491, (1988).
Mackow et al, *Proc. Natl. Acad. Sci. USA*, vol. 87, pp. 518–522, (1990).
Horton et al, *Gene*, vol. 77, pp. 61–68, (1989).
Jones et al, *BioTechniques*, vol. 8, No. 2, pp. 178–183, (1990).
Sarkar et al, *BioTechniques*, vol. 8, No. 4, pp. 404–407, (1990).
Sarkar et al, *Science*, vol. 244, pp. 331–334, (1989).
Smith, et al. (1980) Nucleic Acids Research, vol. 8, p. 2255.

*Primary Examiner*—W. Gary Jones
*Assistant Examiner*—Lisa Arthur
*Attorney, Agent, or Firm*—Oblon, Spivak, McClelland, Maier & Neustadt, P.C.

[57] ABSTRACT

A method is disclosed for the reliable production of proteins by amplifying, transcribing and translating the gene encoding the protein in an essentially cell-free system (gene amplification with transcription/translation, GATT). In the case of dihydrofolate reductase (DHFR), over 1 billion copies of DHFR are produced per original fol gene.

11 Claims, 3 Drawing Sheets

METHOD FOR THE CELL-FREE SYNTHESIS OF PROTEINS

The subject matter disclosed in this document is the product of work supported by the National Institutes of Health, and the United States Government may have some rights in this invention.

BACKGROUND OF THE INVENTION

1. Field of the Invention

This invention relates to the synthesis of proteins by the amplification, transcription and translation of a gene encoding the protein in an essentially cell-free medium.

2. Discussion of the Background

With the advent of the polymerase chain reaction (PCR), one is now able to produce numerous copies of DNA segments in a cell-free system, given an appropriate oligonucleotide sequence with which to start the PCR reaction. (U.S. Pat. Nos. 4,683,195, 4,683,202, and 4,800,159; Saiki et al, *Science*, vol. 230, p. 1350 (1985); Mullis et al, *Methods Enzymo.*, vol. 155p. 335 (1987); Innis et al, "*PCR Protocols: A Guide to Methods and Applications,*" Academic Press New York, (1990); and Saiki et al, *Science*, vol. 239, p. 487 (1988)). Numerous modifications of the PCR reaction and applications to recombinant DNA technology have since been reported.

PCR has been applied to genomic amplification to enhance the sensitivity in sequencing analysis (GAWTS; Stoflet et al, *Science*, vol. 239, p. 491 (1988)) and to facilitate diagnosis Li et al, *Nature*, vol. 335, p. 414 (1988); and Brenner et al, *Biotechniques*, vol. 7, p. 1096 (1989)). PCR has also been utilized to facilitate site-directed mutagenesis (Kadowaki et al, *Gene*, vol. 76, p. 161 (1989); Ito et al, *Gene*, vol. 77, p. 51 (1989); and Hemsley et al, *Nucleic Acids Res.*, vol. 17, p. 6545 (1989)) and recombinant gene preparation studies (Jones et al, *Biotechniques*, vol. 8, p. 178 (1900); and Horton et al, *Gene*, vol. 77, p. 61 (1989)).

In addition, PCR has been exploited to develop a quick subcloning method which has been used in the preparation of the appropriate DNA cassette to insert into an expression vector plasmid for overexpression of a protein in vivo (MacFerrin et al, *Proc. Natl. Acad. Sci. U.S.A.*, vol. 87, p. 1937 (1990)).

Furthermore, generation of mutant protein without any in vivo manipulation has been achieved by incorporating a phage promoter and/or translation initiation signal into a PCR primer. In particular, the preparation of human factor IX fragments, with or without mutation, by a method in which the RNA was amplified by synthesizing the cDNA using reverse transcriptase followed by PCR amplification and then in vitro translation, was demonstrated as a method for sequencing nucleic acid segments from very small quantities of nucleic acids (RAWIT; Sarkar et al, *Science*, vol. 244, p. 331 (1989). No quantitative data for the amount of the translation product were reported.

The PCR reaction has also been applied to a procedure known as DNA amplification-restricted transcription-translation (DARTT; Mackow et al, *Pro. Natl. Acad. Sci. USA*, vol. 87, p. 518 (1990)), wherein PCR is used to amplify DNA segments encoding a series of amino-terminal and/or carboxy-terminal truncated polypeptides of the VP4 outer capsid protein from rhesus rotaviruses as a means for determining the binding sites of the VP4 capsid protein to monoclonal antibodies raised against a number of serologically distinct rotaviruses.

Catalytically active thymidine kinase was synthesized from a cloned vaccinia virus thymidine kinase gene amplified by PCR, then transcribed and translated in vitro, but no quantified data were provided for this procedure (Wilson et al, *Gene*, vol. 77, p. 69 (1989)). Further, a number of other polypeptide by-products were produced during this procedure. These by-products were noted but not discussed. The appearance of numerous byproducts resulting from in vitro translation certainly raises doubt with regard to any inherent predictability of success of in vitro translation alone, much less when used in conjunction with in vitro amplification and transcription.

Thus, there are no reports of the successful production of large quantities of a protein by a method in which PCR gene amplification is coupled with in vitro transcription and translation. In particular, there are no reports of the successful production of a large quantity of a catalytically active enzyme by such a method. Thus, there remains a need for a method of producing large quantities of a protein in a cell-free system.

SUMMARY OF THE INVENTION

Accordingly, one object of the present invention is to provide a method for producing large quantities of a protein by in vitro synthesis.

It is another object of the present invention to provide a method for producing large amounts of a catalytically active enzyme by in vitro synthesis.

It is another object of the present invention to provide a method for producing large quantities of a protein per each original copy of the gene encoding the protein starting from small quantities of the gene encoding the protein.

It is another object of the present invention to provide a method for producing large quantities of dihydrofolate reductase (DHFR) per each original copy of the DHFR gene (fol) by gene amplification with transcription/translation (GATT), starting from minute quantities of genetic material.

It is another object of this invention to provide a method for the production of catalytically active DHFR by the GATT procedure.

It is another object of this invention to provide a method for producing 1 billion or more copies of catalytically active DHFR from each original fol gene by the GATT procedure.

These and other objects, which will become apparent during the following detailed description, have been achieved by the inventor's discovery that a method comprising:

(i) amplifying a DNA segment which contains a gene encoding a protein under the transcriptional control of a phage promoter by the polymerase chain reaction, in vitro, to obtain multiple copies of the DNA segment under the transcriptional control of the promoter;

(ii) transcribing the multiple copies of the DNA segment in vitro, to obtain multiple copies of a RNA segment encoding the protein; and (iii) translating the multiple copies of the RNA segment in vitro, in a cell-free system to obtain the protein;

is an efficient method for producing large quantities of a protein. Thus, the present invention provides a method for gene amplification with transcription/translation (GATT).

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIGS. 2A–2C illustrate the production of dihydrofolate reductase according to the GATT scheme. FIGS. 3A and 3B illustrate the production of DHFR as a function of time and RNA concentration.

DETAILED DESCRIPTION OF THE PREFERRED EMBODIMENTS

Thus, the present invention relates to a method for the in vitro production of large quantities of a protein. Any protein for which the corresponding gene can be obtained may be suitably used in the present method. Such enzymes include enzymes which are industrially useful in the fields of agriculture, beverage production, brewing, detergents, starch and glucose processing, textile manufacture, and waste treatment. Examples of such enzymes include: abzymes amylase, aminoglucosidases, catalases, cellulase, amyloglucuronidase, cellobiase, dextranase, esterases, galactosidase, glucoamylase, beta-glucosidase, glucose isomerase, galactanase, glucanase, glucose oxidase, invertase, isomerase, inulase, lipase, hemicellulase, proteases, proteinase, pectinase, pullulase, oxidases, thermolysin, enzymes for saccharification of maize starch, and carbohydrases.

The present method may also be applied to the production of pharmaceutical proteins, such as albumins, biologically active peptides, blood factors, diagnostic enzymes, growth hormones, human and animal hormones, interferons, monoclonal antibodies, and central nervous system proteins. Examples include: apolipoproteins, alpha-1-antitrypsin (AAT), protein A, calcitonin, complement components, colony stimulating factor, erythropoietin, epidermal growth factor, fibrinogen, fibronectin, gonadotrophin, granulocyte macrophase colony stimulating factor, gamma globulins, histocompatability antigens, insulin, proinsulin, interleukin-2, α- and β-interferon, insulin-like growth factors, luciferase, lymphokines, alpha-1-microglobulin, beta-1-microglobulin, nerve growth factor, proleukin IL-2, somatomedin C, somatostatin, superoxide dismutase, restriction endonucleases, polymerases, TPA, tumor necrosis factor, urokinase, human hormones (such as hFSH, hGH, hLH, hTSH), cancer tumor markers (such as AFP, CEA, PAP, PSE), and human proteins (such as CRP, CPK, LDH, ferritins, HSA, IgE, and IgM).

Some of the above proteins may require post-translational modification, and this may be accomplished by conventional methods known in the art.

As will be shown below, the present method is particularly suitable for the production of large quantities of catalytically active enzymes. It is preferred that the protein be dihydrofolate reductase (DHFR; 5,6,7,8 tetrahydrofolate: $NADP^{30}$ oxidoreductase; E.C. 1.5.1.3). DHFR has been the object of intense research by protein chemists and molecular biologists with respect to the study of enzyme structure/function and gene amplification, because it has a low MW (~18,000 Da), is unprocessed, is water soluble, and is well characterized in regard to its structure, molecular biology, inhibition and functions (see: Kraut, in *Biological Macromolecules and Assemblies*, Jurnak and McPherson, eds., vol. 3, pp. 1–71, Wiley (1989); Johnson in *Folates and Pterins*, Blakely and Benkovic, eds., vol. 1, pp. 581–611, Wiley (1984); Sirotnak et al, *Folate Antagonist as Therapeutic Agents*, vol. 1, Academic (1984); Blakely in *Folates and Pterins*, Blakely and Benkovic, eds., vol. 1, pp. 191–253, Wiley (1984); Schweitzer et al, *FASEB J.*, vol. 4, p. 2441 (1990); Gready, *Adv. Pharmacol. Chemother.*, vol. 17, p. 37 (1980); and Friedkin, *Adv. Enzymol.*, vol. 38, p. 37 (1973). DHFR plays an important role in the biosynthesis of DNA, some amino acids and numerous cellular metabolites. Blocking of DHFR in a growing cell results in a depletion of available 5,6,7,8-tetrahydrofolate (THF), cessation of DNA synthesis and eventual cell death. In view of this, DHFR is a target enzyme in cancer chemotherapy, as well as bacterial, fungal and protozoal infections. The fol gene that encodes *E. coli* DHFR has been sequenced (Smith et al, *Nucleic Acids Res.*, vol. 8, p. 2255 (1980)) and a simple assay for activity has been described by several studies using DHFR enzyme isolated from cells (Poe et al, *Biochemistry*, vol. 11, p. 1023 (1972); Baccanari et al, *Biochemistry*, vol. 20, p. 1710 (1981); and Stone et al, *Biochemistry*, vol. 23, p. 2753 (1984)).

The gene encoding dihydrofolate reductase can be taken from any genetic source of the fol gene. A preferred source of the fol gene is the bacterium *E. coli*.

The gene which encodes the protein to be produced (the target gene) may be placed under the control of the promoter by inserting the target gene into a plasmid which contains a promoter, by conventional recombinant DNA techniques.

Thus, the target gene can be cloned into any suitable plasmid, which will allow in vitro amplification, transcription and translation, in which the transcription of the target gene is under the control of a promoter, preferably the phage T7 promoter. Suitable plasmids include any containing an RNA polymerase promoter such as T7, T3, and SP6. A specific example is pTZ19R (available from U.S. Biochemicals). Insertion of the fol gene into PTZ19R yields the particularly preferred pTZRKE plasmid, in which the *E. coli* fol gene is under the control of the T7 promoter (P. Davanloo, A. H. Rosenberg, J. J. Dunn, and F. W. Studier, *Proc. Natl. Acad. Sci, USA*, vol. 81, 2035 (1984), which is incorporated herein by reference), and which can be used to transform *E. coli* strain JM101 (available from Pharmacia L. K. B.) by standard procedure, e.g. treatment with $CaCl_2$ (Sambrook et al, *Molecular Cloning: Laboratory Manual*, 2nd ed., Cold Spring Harbor Laboratory, Cold Spring Harbor, N.Y. (1989)). Alternatively, the promoter may be fused to the target gene and the resulting fused DNA segment may be inserted into a plasmid, such as puC18. It is also possible to use a DNA segment prepared by the fusion of a promoter and the target gene, which is not inserted into a plasmid, as the template for PCR amplification.

Amplification of the DNA segment in which the target is under the transcriptional control of the promoter can be carried out by the polymerase chain reaction (PCR); see U.S. Pat. Nos. 4,683,195, 4,683,202, and 4,800,159, incorporated herein by reference.

Although the precise conditions used during the PCR amplification step will vary according to the identity of the target gene and the desired level of expression, the reaction is suitable carried out for at least 25 cycles, preferably at least 30 cycles, in which each cycle includes a denaturing step and an extension step, in the presence of a primer. The denaturing step is suitably carried out at a temperature of from 94° to 95° C., and for a time of 1 to 4 min, preferably 1 to 2 min. The extension step is suitably carried out at a temperature of from 72° to 74° C., and for a time of 2 to 4 min. The annealing temperature is 37° to 55° C., preferably 48° to 52° C., and the time is suitably 2 to 4 min. Suitable DNA polymerases include thermally stable DNA polymerases. The preferred DNA polymerase is Taq DNA polymerase.

The in vitro transcription step may be carried out using any suitable transcription system. Such systems include a RNA polymerase, examples of which include T7, SP6, and T3, with the proviso that the RNA polymerase should be compatible with the promoter. Thus, when the target gene is under the transcriptional control of the phage T7 promoter, the RNA polymerase of choice is T7 RNA polymerase. The in vitro transcription reaction is suitably carried out for a time of 1 to 6 hr., at a temperature of 37° C. Of course, the transcription step is carried out in the presence of adequate amounts of GTP, CTP, ATP, and UTP.

The reaction mixture containing the amplified DNA segment obtained by the PCR amplification may be used directly in the transcription step without purification. Alternatively, the DNA segment to be transcribed may be isolated and purified by any conventional technique, e.g., chromatography and/or electrophoresis.

In a preferred embodiment, the mRNA transcripts ay be capped by an appropriate dinucleoside triphosphate analogue. Should capped transcripts be desired, the preferred cap is the diguanosine triphosphate analogue $m^7G(5^1)ppp(5^1)G$.

Any suitable method for in vitro translation and transcription can be employed. The preferred method employs a rabbit reticulocyte lysate system (Pelham et al, *Eur. J. Biochem.*, vol. 67, p. 247 (1976)). In an alternative embodiment, a continuous flow in vitro translation system is employed (Spirin et al, *Science*, vol. 242, p. 331 (1988)). Other suitable translation systems include *E. coli* lysate and wheat germ extract.

The translation reaction may be suitably carried out at a temperature of 30° C., for a time of 0.5 to 9 hr., preferably 3 to 9hr., in the presence of the required amino acids, tRNA, and, optionally, a ribonuclease inhibitor. As in the case of transcription, the translation step may utilize either the crude reaction product obtain from the transcription step or purified RNA obtain by applying conventional purification and isolation techniques, e.g., chromatography and/or electrophoresis, to the crude transcription reaction mixture.

Figure 1:
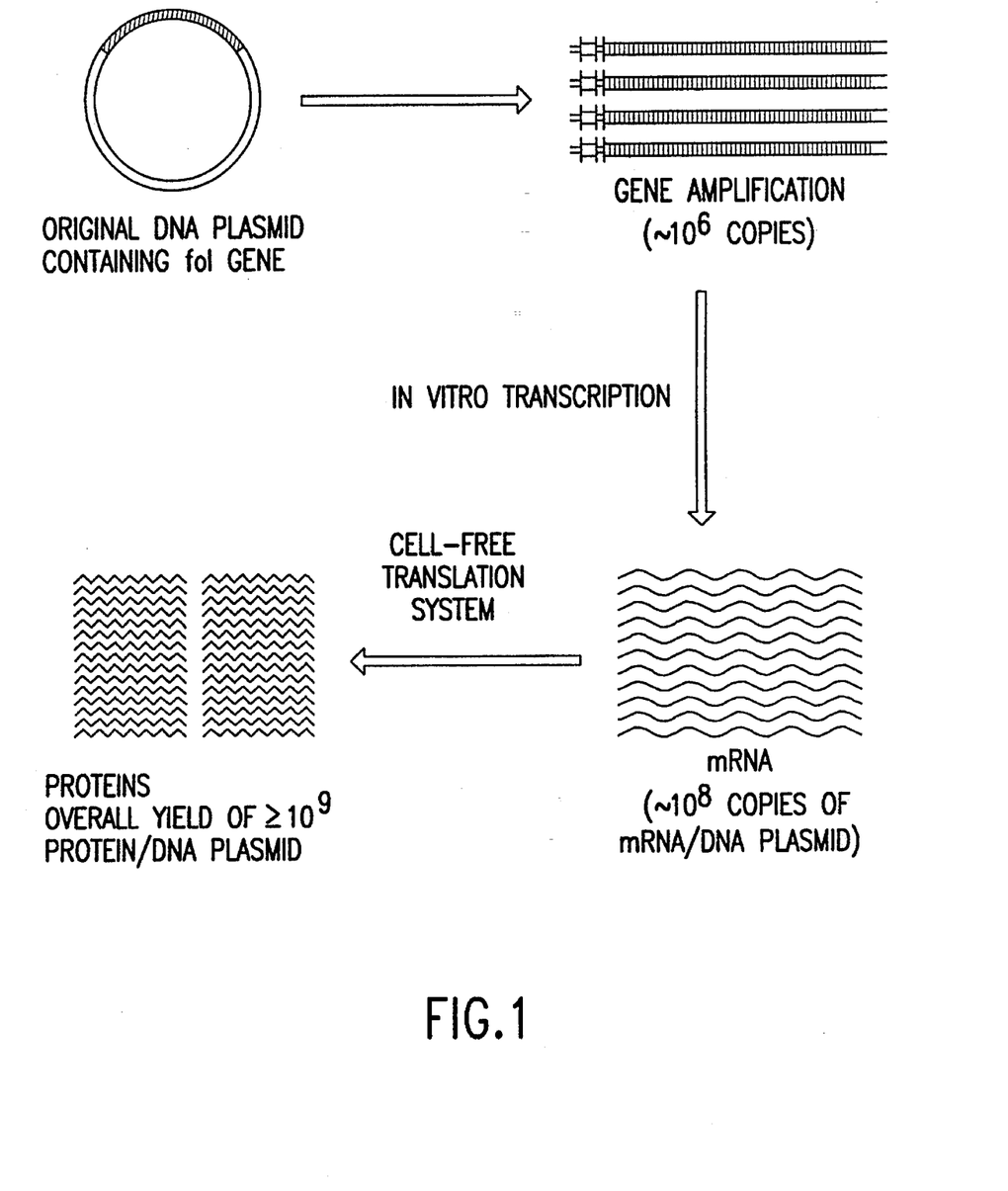
FIG. 1 illustrates a schematic representation of gene amplification with transcription/translation.

Thus, gene amplification, transcription and translation, all conducted in a cell-free system, are the essential features of the GATT procedure. FIG. 1 provides a schematic overview of the GATT procedure as applied to the production of DHFR, wherein from one original plasmid containing the fol gene, amplification, preferably by PCR, yields approximately $10^6$ copies of the fol gene. In vitro transcription of the amplified gene, preferably by phage polymerase and initiated by the phage T7 promoter, creates approximately 100 copies of the mRNA per amplified gene (approximately $10^8$ mRNA/plasmid), then cell-free translation, preferably in a rabbit reticulocyte lysate system, provides $\geq 10^9$ copies of the DHFR protein per original plasmid containing the fol gene. A continuous flow in vitro system provides an additional 100-fold yield of DHFR ($\geq 10^{11}$ copies/original plasmid).

Further, as shown by the results given in Table I, the use of capping in the transcription step results in a dramatic improvement in the yield of protein per copy of mRNA at low mRNA concentrations.

Having generally described this invention, a further understanding can be obtained by reference to the following specific example which is provided herein for purposes of illustration only and is not intended to be limiting unless otherwise specified.

EXAMPLES

Construction of pTZRKE

Plasmid pTZRKE was constructed by cloning the HindIII/BamHI fragment of M13mp8DHFR RK into the same sites on pTZ19R (U.S. Biochemicals). DHFR is under the control of a T7 promoter and retains all of the wild type translation initiation signals (TATA, Shine/Dalgarno, and PribnoW boxes). M13mp8DHFR RK consists of a wild type DHFR gene which has had approximately 400 base pairs of downstream sequence removed, cloned into M13mp8.

A. Amplification.

Plasmid pTZRKE coding the *Escherichia coli* DHFR gene (fol), which was chosen as the target gene in order to quantitatively and unambiguously assess the amplification, transcription, and translation yields and activity assays, was prepared from approximately 107 cells by a micro-scale procedure, which gives enough material (5–15 g) to use in the amplification of the fol gene.

The plasmid for PCR amplification was isolated from *E. coli* strain JM101/pTZRKE by a conventional lysozyme SDS-alkali procedure (Sambrook et al, *Molecular Cloning: Laboratory Manual*, 2nd Ed., Cold Spring Harbor Laboratory, Cold Spring Harbor, N.Y., (1989)). Freshly transformed cells were grown overnight from single colonies at 37° C. in 3 ml SOC media containing 100 µg/ml of ampicillin. The culture was harvested in a 1.5 ml Eppendorf tube, and resuspended in 200 µl of Tris-HCl (pH 8.0), 10 mM EDTA solution containing 200 µg/ml of lysozyme and 100 µg/ml RNAse A. After 10 min. incubation at room temperature, 200 µl of 0.2 N NaOH and 1% SDS were added, and the mixture was gently mixed. Thereafter, 200 µl of 2.6 M KOAc (pH 4.8) was added, and the mixture was centrifuged for 15 min (12,000×g). The supernatant was recovered, extracted with phenol/chloroform, and precipitated with ethanol. After precipitation of the crude DNA by this procedure, resuspension in 10 µl of 10 mM Tris-HCl (pH 7.5), 1 mM EDTA buffer followed by anion-exchange isolation on QIAGEN-tip 20 (available from Qiagen) using the manufacturer's recommended conditions yielded 5–15 g plasmid from 3 mL culture. The isolated plasmid was assayed for purity by 1.0% agarose gel electrophoresis and restriction enzyme digestion analysis.

To generate an amount of DNA sufficient for use in in vitro gene expression, the PCR technique for specifically overproducing a $DNA_{fol}$ fragment was used. The preparative amount of $DNA_{fol}$ fragment was achieved by the use of primers that flank the desired sequence.

The PCR primers were designed using complementary sequences to the pTZRKE sequences within the coding regions starting at the PVU II site (5'-(+)-strand) (ER01) and the BamHI site (3'-(−)-strand) (ER02). Respectively, these sequences are (5')GGCACGACAGGTTTCCCGAC(3') (20-mer) (SEQ ID NO: 1) and (5')CTCTAGAGTCGCCCGATAAGACG(3') (23-mer) (SEQ ID NO: 2). The T7 promoter primer is (5')TAATACGACTCACTATAG(3') (18-mer) (SEQ ID NO: 3). PCR combining the 5'-(+)-strand primer (ER01) and the 3'-(−)-strand primer (ER02) gave a DNA sequence of 791 bp, and PCR combining the T7 promoter primer and the 3'-(−)-strand primer (ER02) gave a DNA sequence of 613 bp.

The primers were synthesized on a Biosearch Model 8600 DNA synthesizer, following the β-cyanoethyl phosphoramidite method. The product DNA primers were purified on a NENSORB column (available from Du Pont), following the suggested conditions of the manufacturer.

The following conditions were employed for the PCR reaction (see Saiki et al, *Science*, vol. 239, p. 487 (1988)): A 100 µl reaction containing pTZ27R was digested by Pvu II (in order to reduce the unspecific product amplification) in 20 mM Tris-HCl, pH 8.4 (at room temperature), 1.5 mM $MgCl_2$, each primer at 1 µM each dATP, dCTP, dGTP, and dTTP at 200 µM 50 mM KCl, 0.1% gelatin and 2 units of Taq DNA polymerase (available from Cetus Perkin-Elmer). The samples were overlaid with approximately 100 µl of mineral oil and subjected to 30 cycles of amplification using a DNA thermal cycler (available from Cetus Perkin-Elmer). The temperatures and incubation times used were as follows: denaturing at 94° C. for 1 minute (4 minutes for the first cycle), annealing at 50° C. for 1.5 minutes, and primer extension at 72° C. for 2 minutes for the first cycle, adding 3 seconds per cycle to the extension time, and for the final cycle, extension of 9 minutes at 72° C.

Figure 2A:
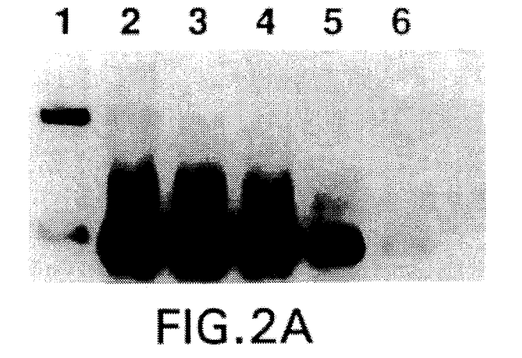
FIG. 2a illustrates the results of electrophoretic analysis of $DNA_{fol}$ (lane 1) and of PCR product synthesized by varying concentrations of pTZRKE in the PCR reaction (44, 11, 2.2, 0.4 and 0.04 fmoles, respectively in lanes 2–6).

After 30 cycles of PCR, the amplified DNA was assessed in a 1% agarose gel containing ethidium bromide as shown in FIG. 2a. The expected electrophoretic band of 791 bp was observed. The amount of amplified $DNA_{fol}$ seemed to be relatively dependent on the original fol gene copy number present in the original template in the range of 0.04 to 44 femtomoles, but not in a linear fashion as expected from early reports (Saiki et al, *Science*, vol. 239, p. 487 (1988)). Amplification of approximately about $10^5$–$10^6$ was obtained for these reactions. A yield of 70–85% efficiency in the PCR reaction was obtained when 1–10ng of template was used for amplifications.

B. Transcription.

A comparison between the ability of pTZRKE and amplified $DNA_{fol}$ to direct the synthesis of biochemically active RNA transcript was carried out.

Transcription was carried out according to a conventional procedure (J. Sambrook, E. F. Fritsch, and T. Maniatis, *Molecular Cloning: Laboratory Manual*, 2nd Ed., Cold Spring Harbor, N.Y. (1989)), in a reaction mixture (volume 20 or 100 µl) containing 40 mM Tris-HCL (pH 7.5), 2 mM spermidine, 6 mM $MgCl_2$, 10 mM dithiothreitol, 10 mM NaCl, 1 unit/µl RNAsin (available from Promega), 500 µM each of GTP, CTP, ATP and UTP, and 0.5 unit/µl of T7 RNA polymerase (Promega) to which the appropriate amount of pTZRKE that had been linearized with BamHI or amplified $DNA_{fol}$ fragment was added as the template. Incubation was conducted at 37° C. for 1–6 hours. In some reactions, transcripts were capped by inclusion of 500 µM of the diguanosine triphosphate analogue $m^7G(5')ppp(5')G$. Run-off RNA transcripts were isolated by QIAGEN-tip 20 column chromatography.

Labeled transcripts were synthesized by adding 50 µCi of [alpha 32P]-CTP to the reaction mixture in order to monitor the transcription yields. Aliquots were electrophoresed on 5% denaturing-PAGE (8 M urea, 90 mM Tris-borate, 2 mM EDTA (pH 8.0) buffer) and visualized by autoradiography. The product yields were estimated by scintillation liquid counting determination.

Figure 2B:
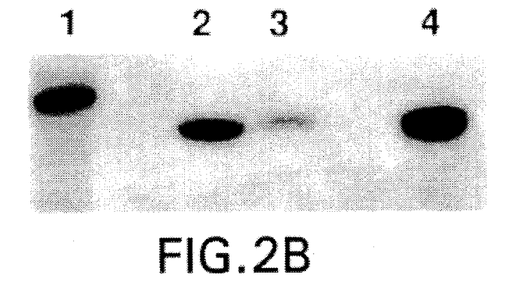
FIG. 2b: 597-nucleotide mRNA (250 and 25 ng in lanes 2 and 3, respectively) in comparison with the mRNA produced by transcription of 0.32 ng of PCR-amplified DNA (lane 4). Lane 1 is a RNA marker 679 nucleotides in length.

The predicted run-off transcripts of 597 nt were produced by amplified DNA (FIG. 2b) as well as the original cloned DNA. The yield from 0.32ng of original DNA after this process was ~1.2×$10^6$ RNA/DNA. After PCR amplification, the reactions yielded up to a 70 fold better ratio. Interestingly, no noticeable transcriptional efficiency differences were observed when the positive coding T7 promoter strand described above was used to amplify $DNA_{fol}$ without the nontranscriptional domain (178 bp) prior to the promoter, in spite of previous studies have demonstrated that Taq DNA polymerase has some 5'→3' exonuclase activity (K. R. Tindall and T. A. Kunkel *Biochemistry*, vol. 27, p. 6008 (1989)) and that T7 RNA polymerase activity is enhanced by the presence of large DNA fragment prior to promoter (S. Tabor, H. W. Huber, and C. C. Richardson, *J. Biol. Chem.*, vol. 262, 16212 (1987)).

C. Translation.

The ability of these synthetic RNA segments to stimulate DHFR biosynthesis was assessed in rabbit reticulocyte lysate system (FIG. 2c) similar to that reported by Pelham et al, *Eur. J. Biochem.*, vol. 67, p. 247 (1976)).

In vitro translation was employed using mRNA-dependent rabbit reticulocyte lysate (available from Promega). The procedures used for the translation reactions in this system were essentially as described by the distributor, except for the final concentration of the component and the final volume. The DHFR synthesis system contained a 58% rabbit reticulocyte lysate extract, 40 µM of each amino acid, except leucine, 20 µM *E. coli*tRNA mixture, 1 unit/µl RNAsin ribonuclease inhibitor (available from Promega), 12 to 18 µM $^3$H-leucine at 110 Ci/mmol (ICN Biochemicals), and 0.1–3.3 µM RNA transcript, or if desired, 2–5 1 unpurified transcription reaction mixture. The translation was conducted at 30° C.

Figure 3A:
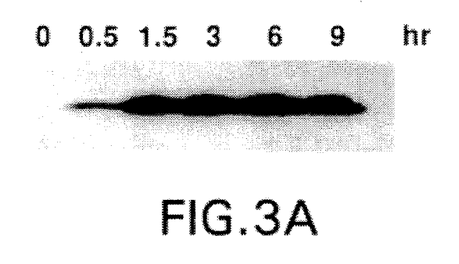
FIG. 3a: time dependence of DHFR production.
Figure 3B:
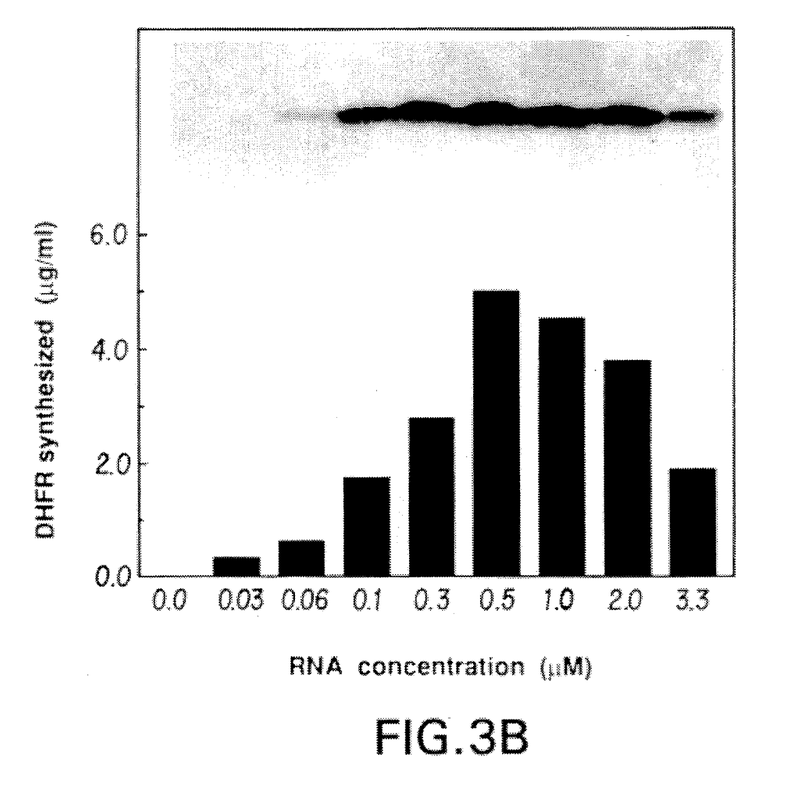
FIG. 3b: DNA concentration dependence of DHFR production.

At various times aliquots of the reaction mixture were removed for analysis of tritiated protein synthesis by SDS-PAGE on gel at 16.5% total acrylamide (% T), 3% in the cross linker bis acrylamide (% C) and 0.1% in SDS using the method of Laemmli, *Nature*, vol. 227, p. 680 (1970). After electrophoresis, the gels were fixed with a solution of 10% acetic acid and 50% methanol. Gels were prepared by fluorography as described Chamberlain, *Anal. Biochm.*, vol. 98, p. 132 (1979). The dried gels were subjected to exposure with Kodak XAR-2-X-ray film at −80° C. for 5 to 14 hours. Translation efficiency was assayed by measuring the level of [$^3$H]-leucine incorporation into the DHFR electrophoretic band by scintillation liquid counting determination. The results are shown in FIG. 3a.

Figure 2C:
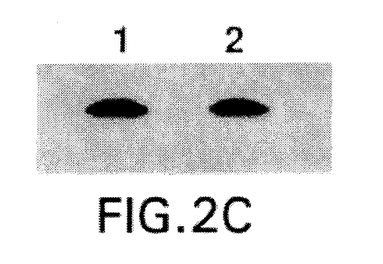
FIG. 2c: dihydrofolate reductase $DNA_{fol}$; product from unamplified (lane 1) or amplified (lane 2) DNAfol.

This eukaryotic system was selected because of its superior messenger sensitivity, high synthetic rate, low background and high mRNA and protein stability. An early result was observed that the pTZRKE-transcript encoding an *E. coli* gene stimulated the cell-free protein biosynthesis in the reticulocyte system as well as or better than in an *E. coli* system. Protein synthesis was assayed initially by measuring the incorporation of [$^3$H]-leucine into polypeptide products and their molecular weight composition on SDS-polyacrylamide gels. As shown in FIG. 2c, protein synthesis occurred only in response to the RNA's from amplified and unamplified plasmids. The polypeptide products migrated at a relative molecular weight of 18,000 Da, as expected for DHFR. Quantitative analysis of the radioactivity in the DHFR band on a polyacrylamide gel provided a measure of the amount of DHFR synthesized, because the leucine content of this enzyme is known. Under the conditions employed, 0.4–0.5 DHFR molecule was produced for each synthetic RNA transcript used in the incubation.

The appearance of DHFR was shown to exhibit a "biphasic" dependence on the concentration of mRNA added to the protein biosynthesis system (FIG. 2a). When the RNA concentration employed during protein synthesis was increased from 1.5 to 3.0 µM a decrease in the appearance of the DHFR band was noted. This effect was reproducible in three independent experiments.

Also investigated was the effect of polyamines and $Mg^{2+}$ on the extent of the protein biosynthesis, because these factors have been reported to improve both the level and fidelity of translation in cell-free systems (Pelham et al, *Eur. J. Biochem.*, vol. 67, p. 247 (1976); and Yarus et al, *Gene Function in Prokaryotes*, Beckwith, Davies, & Gallant, eds., pp. 23–63, Cold Spring Harbor Laboratory, Cold Spring Harbor, N.Y. (1983) and references cited therein). Interestingly, in the present experiments, using concentrations of spermidine up to 0.5 mM had no significant effect on the biosynthesis of DHFR, but inclusion of concentrations greater than 1 mM of spermidine or 0.8 mM of $Mg^{2+}$ decreased the observed polypeptide band on the polyacrylamide gel fluorogram. Using the optimal conditional found for the present system, it was observed that the protein synthesis appeared in a time dependent fashion with maximal synthesis occurring after 90 minutes (FIG. 3a). The stability of the protein was observed as constant up to 10 hours.

The cap structure 7mG(5')ppp(5')G has been reported to enhance the protein biosynthesis in eukaryotic systems. Two of the important roles of the 5' Cap structure are to facilitate ribosome binding during the initiation phase of translation in eukaryotic systems (Banerjee et al, *Microbiol. Rev.*, vol. 44, p. 175 (1980); Fillipowicz, *FEBS Lett.*, vol. 96, p. 1 (1978); and Shatkin, *Cell*, vol. 40, p. 223 (1985)) and to stabilize the RNA against 5'-exonucleolytic activity (Green et al, *Cell.*, vol. 32, p. 681 (1983)). When amplified $DNA_{fol}$ product was transcribed in the presence of Cap analog 7mGpppG, a capped RNA was synthesized. Stimulation of 6–10 fold greater protein synthesis was produced by capped RNA than uncapped transcript when 0.025 or 0.10 µM RNA was added (see Table I). Under these conditions, up to 31 DHFR molecules were produced per mRNA; equivalent to 0.7–2.7 billion ($10^8$) copies of protein per original fol gene copy isolated from the cells. It is interesting to note that the "biphasic" shape of RNA-dependence was displaced to lower quantities of RNA. This suggested that the binding of some protein factor (as cap binding protein and initiation factor) can act as a limiting factor in the system. This is in agreement with the report of 150% enhancement in protein translation of *E. coli*tryptophan synthase alpha subunit by increasing the amount of initiation factor in the *E. coli*cell-free biosynthesizing system (Payne et al, *Biochemistry*, vol. 26, p. 3197 (1987)).

TABLE I

Quantitation of Dihydrofolate Reductase Synthesis and Activity. Effect of the *in vitro* Protein Biosynthesis Efficiencies by the Stimulation of the Synthetic $DNA_{fol}$ Transcript Containing Cap analogue.

| mRNA (µM) | Cap-mRNA Incorporate | DHFR Synthesized (µg/mL) | DHFR/mRNA Ratio | DHFR Activity[a] Unit/ml | Specific Activity[b] |
|---|---|---|---|---|---|
| 0.40 | – | 31 | 4.5 | 1.01 | 589 |
|  | + | 30 | 4.5 | 1.02 | 610 |
| 0.10 | – | 15 | 8.8 | 0.46 | 609 |
|  | + | 57 | 31 | 1.85 | 525 |
| 0.25 | – | 1.7 | 3.8 | 0.05 | 525 |
|  | + | 13 | 30 | 0.46 | 633 |

[a]Determined spectrophotometrically.
[b]Specific activity is expressed as DHF reduced per min per enzyme molecule, a total average of 580 ± was estimate and is in good agreement with the expected value.

Spectrophotometric assays for DHFR activity were carried out according to conventional procedures (Poe et al, *Biochemistry*, vol. 11, p. 1023 (1972).

In a reaction mixture (0.5–0.9 mL) containing 50 mM Tris-HCl (pH 7.4) 50 mM KCl, 10 µmM β-mercaptoethanol, 100 µM NADPH, and 100 µM 7,8-dihydrofolate (DHF). Assays were performed either at room temperature or 37° C. in a Perkin Elmer Lambda Array spectrophotometer. One enzyme unit is defined as the amount of enzyme required to reduce 1 µmole of DHF/min using a molar extinction coefficient of 11,650 $M^{-1}$ $cm^{-1}$ at 340 nm for the redox reaction of the DHF and NADPH (Kaufman et al, *J. Biol. Chem.*, vol. 241, p. 1319 (1968)) at room temperature or 12,300 $M^{-1}$ $cm^{-1}$ at 37° C. (Hillcoat et al, *Anal Biochem.*, vol. 21, p. 178 (1967)). Each reaction was stimulated by an aliquot of protein biosynthesis reaction mixture (5–15 µL) after 10 min centrifugation (12,000×g) or isolated protein. The specific activity of DHFR is 50 units/mg protein (Villafranca et al., *Science*, vol. 222, p. 782 (1983)).

The appearance of a protein capable of catalyzing the conversion of 7,8-dihydrofolate (DHF) to 5,6,7,8-tetrahydrofolate (THF) was measured by a spectrophotometric method involving the decrease in absorbance that occurs at 340 nm when NADPH is reacted to form $NADP^+$. The activities of 0.5–1.9 mol DHF reduced/min per mL of reaction mixture obtained (Table I) gave a yield of 94–98% of the predicted value obtained by the correlation of the incorporation of $^3$H-leucine into the DHFR fluorographic band on a polyacrylamide gel.

Although it has been demonstrated that PCR-amplified DNA can be used directly to direct enzyme RNA transcription followed by in vitro translation, it has also been noted that no overall yield or protein activity has been reported. In addition, some transcripts were translated with reduced efficiency producing an incomplete polypeptide product, presumably resulting from premature transcriptional termination and RNA or protein degradation.

These difficulties have been overcome by the present translation system for the expression of the transcript, in which good stability of the product is observed for up to ten hours (FIG. 3a). In the present case, protein biosynthesis with biochemical activity was clearly stimulated directly from the amplified PCR products. Several different colonies were used in the GATT procedure without any purification between DNA crude preparation, PCR amplification, and T7 RNA polymerase transcription. GATT was applied basically as described above for six different colonies except that the crude DNA preparations (10–500ng) were used directly for PCR without further purification. The amplification reaction mixtures were used to synthesize the $DNA_{fol}$ transcript, and this mixture was used for the stimulation of DHFR synthesis in the rabbit reticulocyte system. The yield was $2.4\pm0.5\times10^9$ DHFR synthesized per original DNA molecule as calculated after quantification of the tritiated DHR protein as described above. No translational product differences were attributable to using the transcriptional reaction mixture or purified transcripts in the translational reaction. However, it should be noted that this result is not necessarily inconsistent with the report that it is important to eliminate certain inhibitors present in the PCR reactions before in vitro translation.

As described above, a particular advantage of the present GATT method in the studies of the protein/structure relationship is that it allows practically all the molecular cloning strategies in a cell-free system. The present study demonstrates the ability to synthesize catalytically active protein enzymes in a cell-free system and particularly demonstrates that enzymatically amplified DNA products can be used directly to stimulate the in vitro transcription/translation of active biomolecules without the need to incorporate the amplified DNA into a plasmid vector or in vivo manipulation as previously required.

The present method has been exemplified by the DHFR preparation as a model system. However, virtually any gene from any cell may be selected. In addition, the entire procedure from the isolation of the original genetic material to obtaining the protein can be completed in days instead of several weeks by the classical methods. Thus, the preparation of mutant genes by site-directed mutagenesis using the PCR method can be analyzed much faster and simpler with the aid of the present method.

Obviously, numerous modifications and variation of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for producing a water-soluble protein, consisting essentially of:
   (i) amplifying a DNA segment consisting essentially of a gene encoding said water-soluble protein under the transcriptional control of a phage promoter, by the polymerase chain reaction, in vitro, to obtain multiple copies of said DNA segment which contains said gene under transcriptional control of said promoter;
   (ii) transcribing without purification said multiple copies of said DNA segment in vitro, to obtain multiple copies of a RNA segment which encodes said water-soluble protein; and
   (iii) translating without purification said multiple copies of said RNA segment, in vitro, to obtain at least one billion copies of said water-soluble protein per original DNA segment.

2. The method of claim 1, wherein said protein is dihydrofolate reductase.

3. The method of claim 1, wherein said translating is conducted using a rabbit reticulocyte lysate system.

4. The method of claim 1, wherein said translating is conducted using a continuous flow translation system.

5. The method of claim 1, wherein said gene encodes dihydrofolate reductase and is isolated from *Escherichia coli*.

6. The method of claim 1, wherein said promoter is a phage T7 promoter.

7. The method of claim 1, wherein during said transcribing said RNA is capped with $m^7G(5')ppp(5')G$.

8. The method of claim 1, wherein said water-soluble protein is unprocessed.

9. The method of claim 4, wherein at least $10^{11}$ copies of said water-soluble protein are produced after said translating step.

10. The method of claim 2, wherein at least $10^{11}$ copies of said water-soluble protein are produced after said translating step.

11. A method for producing a water-soluble protein, consisting essentially of:
    (i) amplifying a DNA segment consisting essentially of a gene encoding said water-soluble protein under the transcriptional control of a phage promoter by the polymerase chain reaction in vitro to obtain multiple copies of said DNA segment which contains said gene under transcriptional control of said promoter;
    (ii) transcribing without purification said multiple copies of said DNA segment in vitro to obtain a crude product comprising multiple copies of a RNA segment which encodes said water-soluble protein; and
    (iii) translating said crude product in vitro to obtain at least one billion copies of said water-soluble protein per original DNA segment.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GGCACGACAG GTTTCCCGAC                                               20

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CTCTAGAGTC GCCGGATAAG ACG                                           23

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

TAATACGACT CACTATAG                                                 18